United States Patent
Park (10) Patent No.: US 10,015,470 B2
(45) Date of Patent: Jul. 3, 2018

(54) ROBOT FOR REPOSITIONING PROCEDURE, AND METHOD FOR CONTROLLING OPERATION THEREOF

(71) Applicant: KYUNGPOOK NATIONAL UNIVERSITY INDUSTRY-ACADEMIC COOPERATION FOUNDATION, Daegu (KR)

(72) Inventor: Il-hyung Park, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 1 day.

(21) Appl. No.: 14/443,027

(22) PCT Filed: Nov. 15, 2013

(86) PCT No.: PCT/KR2013/010387
§ 371 (c)(1),
(2) Date: May 14, 2015

(87) PCT Pub. No.: WO2014/077613
PCT Pub. Date: May 22, 2014

(65) Prior Publication Data
US 2015/0341615 A1    Nov. 26, 2015

(30) Foreign Application Priority Data

Nov. 16, 2012  (KR) .................. 10-2012-0130543

(51) Int. Cl.
*G06K 9/00*    (2006.01)
*H04N 13/02*    (2006.01)
(Continued)

(52) U.S. Cl.
CPC ........... *H04N 13/021* (2013.01); *A61B 17/66* (2013.01); *A61B 34/30* (2016.02); *B25J 9/1671* (2013.01);
(Continued)

(58) Field of Classification Search
CPC ........ A61B 17/06166; A61B 2034/101; A61B 2090/376; A61B 34/30; A61B 17/151;
(Continued)

(56) References Cited

U.S. PATENT DOCUMENTS 5,546,942 A * 8/1996 Zhang ...................... A61F 5/04
                                                                          600/427
5,799,055 A    8/1998 Peshkin et al.
(Continued)

FOREIGN PATENT DOCUMENTS

JP    2000510730 A    8/2000
JP    2003180701 A    7/2003
(Continued)

OTHER PUBLICATIONS

Sahiti et al ("Finite element analysis of femur in the evaluation of Osteoporosis", Department of Biomedical Engineering, SRM University, India, IEEE 2011, pp. 415-419).*
(Continued)

*Primary Examiner* — Amara Abdi
(74) *Attorney, Agent, or Firm* — Ohlandt, Greeley, Ruggiero & Perle, LLP (57) ABSTRACT

Disclosed is a robot for a repositioning procedure. The robot for a repositioning procedure according to the present invention, comprises: a photographing unit for photographing a plurality of bone images at different angles for each fracture region of a patient and normal region corresponding to the fracture region; an image processing unit for generating a three-dimensional interpolation image for each fracture
(Continued)

region and normal region using the plurality of photographed bone images; and a display unit for displaying both the generated three-dimensional interpolation image for the fracture region and the generated three-dimensional interpolation image for the normal region.

24 Claims, 11 Drawing Sheets

(51) Int. Cl.
| | |
|---|---|
| *G06T 7/00* | (2017.01) |
| *G06K 9/62* | (2006.01) |
| *G06K 9/46* | (2006.01) |
| *G06T 7/20* | (2017.01) |
| *B25J 9/16* | (2006.01) |
| *B25J 11/00* | (2006.01) |
| *A61B 17/66* | (2006.01) |
| *A61B 34/30* | (2016.01) |
| *G06T 7/12* | (2017.01) |
| *G06T 7/62* | (2017.01) |
| *A61B 6/00* | (2006.01) |
| *A61B 90/00* | (2016.01) |
| *H04N 13/00* | (2018.01) |

(52) U.S. Cl.
CPC ........... *B25J 9/1679* (2013.01); *B25J 11/009* (2013.01); *G06K 9/46* (2013.01); *G06K 9/6201* (2013.01); *G06T 7/0012* (2013.01); *G06T 7/12* (2017.01); *G06T 7/20* (2013.01); *G06T 7/62* (2017.01); *A61B 6/505* (2013.01); *A61B 2090/364* (2016.02); *G06K 9/00208* (2013.01); *G06K 2009/4666* (2013.01); *G06T 2207/10081* (2013.01); *G06T 2207/10088* (2013.01); *G06T 2207/10116* (2013.01); *G06T 2207/20221* (2013.01); *G06T 2207/30008* (2013.01); *H04N 13/0011* (2013.01); *H04N 13/0014* (2013.01)

(58) Field of Classification Search
CPC ....... A61B 17/152; A61B 17/66; A61B 34/10; A61B 34/25; A61B 6/505; G06T 2210/41; G06T 2207/10081; G06T 2207/10088; G06T 2207/10116; G06T 2207/20221; G06T 2207/30008; G06T 7/0012; G06T 7/0042; B25J 11/009; B25J 9/1671; B25J 9/1679; H04N 13/021
See application file for complete search history.

(56) References Cited

U.S. PATENT DOCUMENTS

| | | | | |
|---|---|---|---|---|
| 6,069,932 | A | | 5/2000 | Peshkin et al. |
| 6,198,794 | B1* | | 3/2001 | Peshkin ................. A61B 6/464 378/42 |
| 7,835,559 | B1* | | 11/2010 | Schurman .............. G01N 23/04 250/390.02 |
| 8,838,205 | B2 | | 9/2014 | Shoham et al. |
| 8,870,799 | B2* | | 10/2014 | Reiley ................. A61F 5/05841 602/16 |
| 9,872,733 | B2* | | 1/2018 | Shoham ................. A61B 34/70 |
| 2002/0045812 | A1* | | 4/2002 | Ben-Haim ........... A61B 5/0215 600/407 |
| 2002/0194023 | A1 | | 12/2002 | Turley et al. |
| 2004/0068187 | A1* | | 4/2004 | Krause ................... A61B 17/15 600/443 |
| 2006/0098851 | A1* | | 5/2006 | Shoham ............. A61B 17/1703 382/128 |
| 2006/0100498 | A1* | | 5/2006 | Boyce .................... A61B 6/505 600/408 |
| 2007/0208234 | A1* | | 9/2007 | Bhandarkar ........... A61B 19/52 600/300 |
| 2009/0015680 | A1* | | 1/2009 | Harris ...................... A61B 1/04 348/208.1 |
| 2009/0054910 | A1* | | 2/2009 | Zheng ................ A61B 17/1703 606/130 |
| 2009/0110748 | A1* | | 4/2009 | Okada .................... A61K 33/42 424/602 |
| 2010/0046704 | A1* | | 2/2010 | Song ....................... G01N 23/04 378/57 |
| 2010/0172571 | A1 | | 7/2010 | Yoon et al. |
| 2011/0033516 | A1* | | 2/2011 | Markwald ............. A61L 27/227 424/422 |
| 2011/0313479 | A1* | | 12/2011 | Rubin ................... A61B 6/5235 607/1 |
| 2012/0083696 | A1* | | 4/2012 | Kitamura .................. G06T 7/33 600/443 |
| 2012/0293627 | A1* | | 11/2012 | Ishii .................... H04N 13/0011 348/46 |
| 2013/0345718 | A1* | | 12/2013 | Crawford ............. A61B 17/025 606/130 |
| 2014/0051922 | A1* | | 2/2014 | Guthart .................... A61B 8/12 600/103 |
| 2014/0185742 | A1* | | 7/2014 | Chen ...................... G01V 5/005 378/5 |
| 2015/0112344 | A1 | | 4/2015 | Shoham et al. |

FOREIGN PATENT DOCUMENTS

| | | | |
|---|---|---|---|
| JP | 2003339725 A | 12/2003 | |
| JP | 2005529667 A | 10/2005 | |
| JP | 2011172977 A | 9/2011 | |
| JP | 2013-094930 * | 5/2013 | ............. B25J 15/04 |
| KR | 10-2000-0011134 | 2/2000 | |
| KR | 10-2010-0081588 | 7/2010 | |
| WO | 2003105659 | 12/2003 | |

OTHER PUBLICATIONS

International Search Report dated Mar. 31, 2014 corresponding to Korean Application No. PCT/KR2013/010387; 2 pages.
Written Opinion dated Mar. 31, 2014 corresponding to Korean Application No. PCT/KR2013/010387; 2 pages.
Japanese Office Action dated Jul. 25, 2017 for Japanese application No. 2015-542951.

* cited by examiner

ROBOT FOR REPOSITIONING PROCEDURE, AND METHOD FOR CONTROLLING OPERATION THEREOF

TECHNICAL FIELD

The present general inventive concept generally relates to providing a robot for a repositioning procedure and a method of controlling an operation thereof, and more particularly, to providing a repositioning procedure robot capable of displaying a fracture region along with a three-dimensional interpolation image of a symmetric position where a fracture does not occur, and a method of controlling an operation thereof.

BACKGROUND ART

A robot refers to a mechanical device that is made so as to perform several hard and difficult jobs instead of a human. The robot has been recently applied in industrial and medical fields.

Since robot technologies that are used in medical fields enables more precise medical surgeries, a surgical robot has steeply extended. However, the robot technologies have been applied and commercialized only in a celioscope field and a joint replacement surgical field not in fracture and muscloskeletal reconstruction technologies.

However, fracture and muscloskeletal reconstruction surgeries have recently increased due to an increase in an aging population, and thus there is a need for a development of a robot technology that may be used in fracture and musclo-skeletal reconstruction surgeries.

DETAILED DESCRIPTION OF THE INVENTION

Technical Problem

Therefore, the present general inventive concept provides a repositioning procedure robot capable of displaying a fracture region along with a three-dimensional interpolation image of a symmetric position where a fracture does not occur, and a method of controlling an operation thereof.

Technical Solution

According to an aspect of the exemplary embodiments, there is provided a robot for a repositioning procedure, including: a photographing unit configured to capture a plurality of bone images of a fracture region and a normal region corresponding to the fracture region of a patient at different angles; an image processor configured to generate three-dimensional interpolation images of the fracture region and the normal region by using the plurality of bone images; and a display unit configured to display the three-dimensional interpolation image of the fracture region and the three-dimensional interpolation image of the normal region together.

The photographing unit may capture the fracture region and the normal region by using at least one device selected from X-ray, MRI, and CT.

The image processor may extract diaphyses of the bone images and generate a three-dimensional interpolation image of the extracted diaphyses.

The image processor may generate the three-dimensional interpolation image in consideration of at least one selected from diameters, bending degrees, and lengths of the bone images.

The robot may further include a position sensor configured to sense a position of a movable bone region of the fracture region. The display unit nay overlap the three-dimensional interpolation image of the fracture region on the three-dimensional interpolation image of the normal region based on the sensed position.

The robot may further include a matching unit configured to extract bone outlines of the three-dimensional interpolation image of the fracture region and the three-dimensional interpolation image of the normal region and calculate a matching degree between the extracted bone outlines. The display unit may display the calculated matching degree.

The matching unit may divide the three-dimensional interpolation image into a plurality of regions and calculate matching degrees between bone outlines of the plurality of regions.

The robot may further include: a driver configured to be fixed onto a side of the movable bone region of the fracture region and move the movable bone region; and a manipulator configured to receive a control command for controlling an operation of the driver.

The manipulator may receive a stop command as a control command, and in response to the stop command being input, the driver may keep a position of the movable bone region in a current state.

The robot may further include: a path calculator configured to calculate a movement path for repositioning the movable bone region of the fracture region; and a controller configured to stop an operation of the driver in response to the movable bone region straying from the calculated movement path.

The driver may be connected to a side of the movable bone region through a fixing pin, a connection part, and an external fixing part.

The fixing pin may include a spiral region that is inserted into a fractured bone region and a threshold region that protrudes to enable the spiral region to be inserted only into a preset depth.

An outer shape of the threshold renion may be a polygonal shape based on a central axis of the fixing pin.

The connection part may include a first region that fixes the fixing pin on a side and a second region that fixes the external fixing part on an other side.

The external fixing part may have at least one selected from a U shape, a ring shape, a semicircular shape, and a linear shape.

According to another aspect of the exemplary embodiments, there is provided a method of controlling an operation of a robot for a repositioning procedure, the method including: capturing a plurality of bone images of a fracture region and a normal region corresponding to the fracture region of a patient at different angles; generating three-dimensional interpolation images of the fracture region and the normal region by using the plurality of bone images; and displaying the three-dimensional interpolation image of the fracture region and the three-dimensional interpolation image of the normal region together.

The fracture region and the normal region may be captured by using at least one device selected from X-ray, MRI, and CT.

Diaphyses of the bone images may be extracted, and a three-dimensional interpolation image of the extracted diaphyses may be generated.

The three-dimensional interpolation image may be generated in consideration of at least one selected from diameters, bending degrees, and lengths of the bone images.

The method may further include: sensing a position of a movable bone region of the fracture region. The three-dimensional interpolation image of the fracture region may overlap on the three-dimensional interpolation image of the normal region based on the sensed position.

The method may further include: extracting bone outlines of the three-dimensional interpolation image of the fracture region and the three-dimensional interpolation image of the normal region and calculating a matching degree between the extracted bone outlines. The calculated matching degree may be displayed.

The three-dimensional interpolation image may be divided into a plurality of regions, and matching degrees between bone outlines of the plurality of regions may be calculated.

The method may further include: receiving a control command for controlling an operation of the robot: and moving a movable bone region of the fracture region according to the control command.

The receiving of the control command may include: receiving a stop command. The moving the movable bone region may include: keeping a position of the movable bone region in a current state in response to the stop command being received.

The method may further include: calculating a movement path for repositioning the movable bone region of the fracture region: and stopping an operation of the robot in response to the movable bone region straying from the calculated movement path.

MODE FOR INVENTION

The present general inventive concept will now be described in more detail with reference to the attached drawings.

Figure 1:
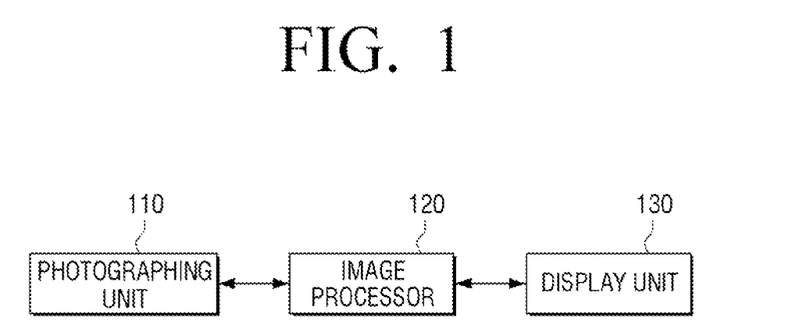
FIG. 1 is a brief block diagram illustrating a robot for a repositioning procedure according to an exemplary embodiment of the present general inventive concept.

FIG. 1 is a brief block diagram illustrating a robot for a repositioning procedure according to an exemplary embodiment of the present general inventive concept.

Referring to FIG. 1, a repositioning procedure robot 100 includes a photographing unit 110, an image processor 120, and a display unit 130.

The photographing unit 110 captures a plurality of bone images at different angles for each of a fracture region and a normal region corresponding to the fracture region of a patient. In detail, the photographing unit 110 may rotate on each of the fracture region and the normal region corresponding to the fracture region of the patient to capture the plurality of bone images by using technologies such as an X-ray, an MRI, and CT that may capture a bone. Here, the normal region may be a bone region facing a bone positioned in the fracture region, e.g., may be a right femoral bone if the fracture region is a left femoral bone.

Here, the same region is captured at different angles because it is difficult to check a rotation state of a bone, etc. if a fracture reposition is checked by using only a two-dimensional image. Therefore, in the present exemplary embodiment, the same region is captured at different angles, and the image processor 120 that will be described later performs a three-dimensional interpolation by using bones images that are captured at different angles.

The image processor 120 generates interpolation images of the fracture region and the normal region by using the plurality of bone images that are captured. In detail, the image processor 120 may generate a three-dimensional interpolation (hereinafter referred to as a three-dimensional fracture image) of the fracture region and a three-dimensional interpolation image (hereinafter referred to as a three-dimensional normal image) of the normal region by using the plurality of bone images that are captured. A more detailed method of generating interpolation images will be described later with reference to FIG. 6.

The image processor 120 may perform image-processing on the generated three-dimensional interpolation images according to a position of a bone that is sensed by a sensor 140 that will be described later. In detail, a bone of the fracture region is moved by a repositioning procedure. Therefore, the image processor 120 may vary a position of a movable region on a three-dimensional image to generate a three-dimensional fracture image according to a movement degree of a bone that is sensed by the sensor 140.

The display unit 120 displays various types of information that are provided from the repositioning procedure robot 100.

Figure 7:
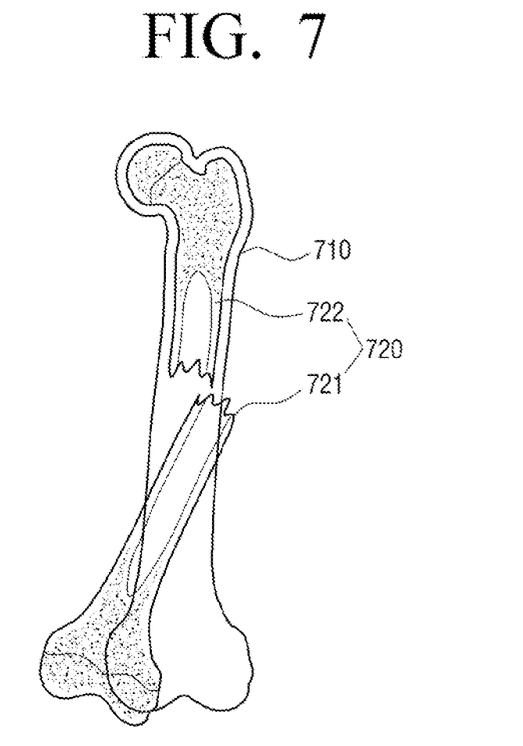
FIGS. 7 through 9 are views illustrating a user interface (UI) window that is displayed on a display unit of FIG. 1, according to various exemplary embodiments of the present general inventive concept.
Figure 9:
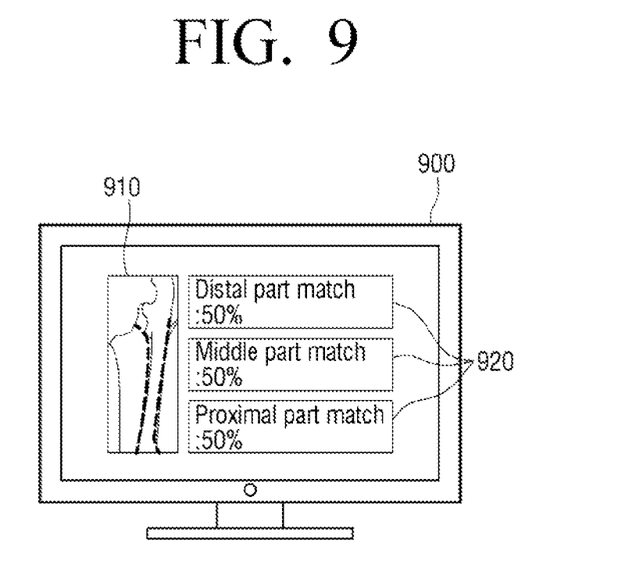

The display unit 120 displays the generated three-dimensional interpolation image (i.e., a three-dimensional fracture image) of the fracture region and the three-dimensional interpolation image (i.e., a three-dimensional normal image) of the generated normal region. Here, the display unit 120 may overlap the three-dimensional fracture image on the three-dimensional normal image as shown in FIG. 7. Also, the display unit 120 may display a matching degree calculated by a matching unit, which will be described later, as shown in FIG. 9. Various types of UI windows that may be displayed on the display unit 120 will be described later with reference to FIGS. 7 through 9.

As described above, the repositioning procedure robot 100 according to the present exemplary embodiment generates and displays the three-dimensional interpolation images of the fracture region and the normal region corresponding to the fracture region. Therefore, a doctor may perform a more precise repositioning procedure.

As described above, the photographing unit 110, the image processor 120, and the display unit 130 are applied to only the repositioning procedure robot 100. However, structures of the photographing unit 110, the image processor 120, and the display unit 130 may be realized as a diagnostic device for measuring a fracture degree of the patient.

Only brief elements of the repositioning procedure robot 100 have been described and illustrated above, but the repositioning procedure robot 100 may further include other elements besides the above-described elements. A more detailed structure of the repositioning procedure robot 100 will now be described with reference to FIG. 2.

Figure 2:
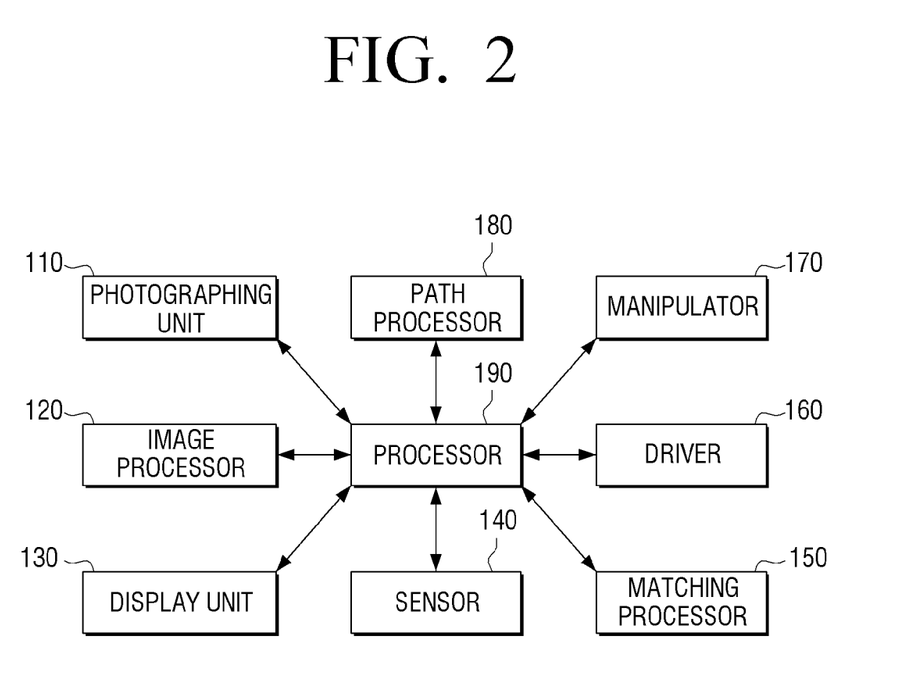
FIG. 2 is a detailed block diagram illustrating a robot for a repositioning procedure according to an exemplary embodiment of the present general inventive concept.

FIG. 2 is a detailed block diagram illustrating a repositioning procedure robot according to an exemplary embodiment of the present general inventive concept.

Referring to FIG. 2, the repositioning procedure robot 100 may include the photographing unit 110, the image processor 120, the display unit 130, the sensor 140, a matching unit 150, a driver 160, a manipulator 170, a path calculator 180, and a controller 190.

Detailed functions and operations of the photographing unit 110, the image processor 120, and the display unit 130 are the same as described with reference to FIG. 1, and thus their repeated descriptions are omitted.

The sensor 140 senses a position of a movable bone region of a fracture region. In detail, the repositioning procedure robot 100 moves the movable bone region of the fracture region to reposition a bone. However, a bone position of the fracture region is changed by this movement, and thus a performance degree of this movement needs to be checked. In an existing art, a state of a bone depending on such a movement is checked through additional X-ray capturing. However, in the present exemplary embodiment, markers may be respectively installed in a fixed region and a movable region of a fracture region, and the sensor 140 may track the marker installed in the movable region to sense a position of a movable bone region. As described above, the sensor 140 may be used to move and track the movable bone region of the fracture region without X-ray capturing.

The matching unit 150 respectively extracts bone outlines from the generated three-dimensional interpolation images of the fracture region and the normal region and calculates a matching degree between the bone outlines.

The matching unit 150 may also divide the three-dimensional interpolation image into a plurality of regions and matching degrees between outlines of the plurality of regions. In detail, the matching unit 150 may the three-dimensional interpolation image into an upper region, a middle region, and a lower region and individually calculate matching degrees of the upper, middle, and lower regions. As described above, a three-dimensional interpolation image may be divided into a plurality of regions to calculate matching between bones so as to check whether there has been rotation, reduction or overtraction of a whole bone.

In the above description, a bone outline is extracted from a three-dimensional interpolation image, and matching degree between two bones is calculated by using the extracted bone outline. However, the matching degree between the two bones may be calculated by using various types of parameters such as volumes, areas, etc. of bones.

The calculated matching degree between the two bones as described above may be displayed on the display unit 130 that has been described above. Also, the calculation of the matching degree may be performed in real time according to movements of the bones.

Figure 3:
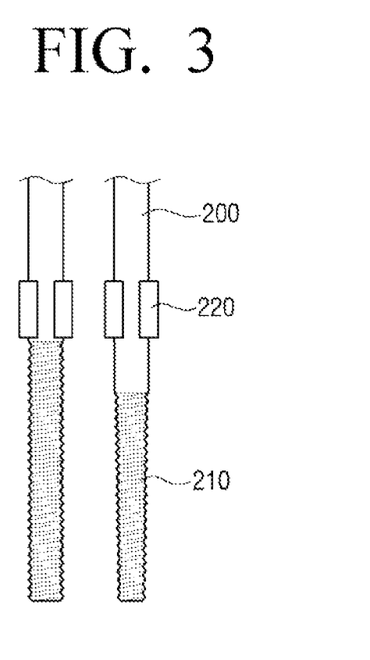
FIG. 3 is a view illustrating a shape of a fixing pin according to an exemplary embodiment of the present general inventive concept.
Figure 4:
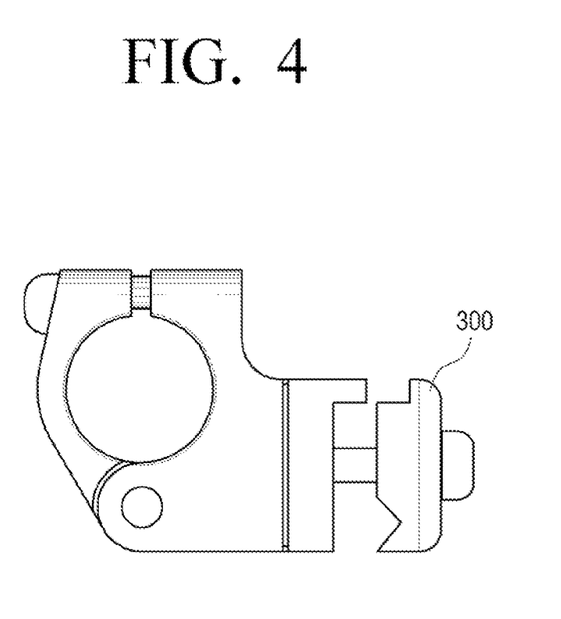
FIG. 4 is a view illustrating a shape of a connection part according to an exemplary embodiment of the present general inventive concept.
Figure 5:
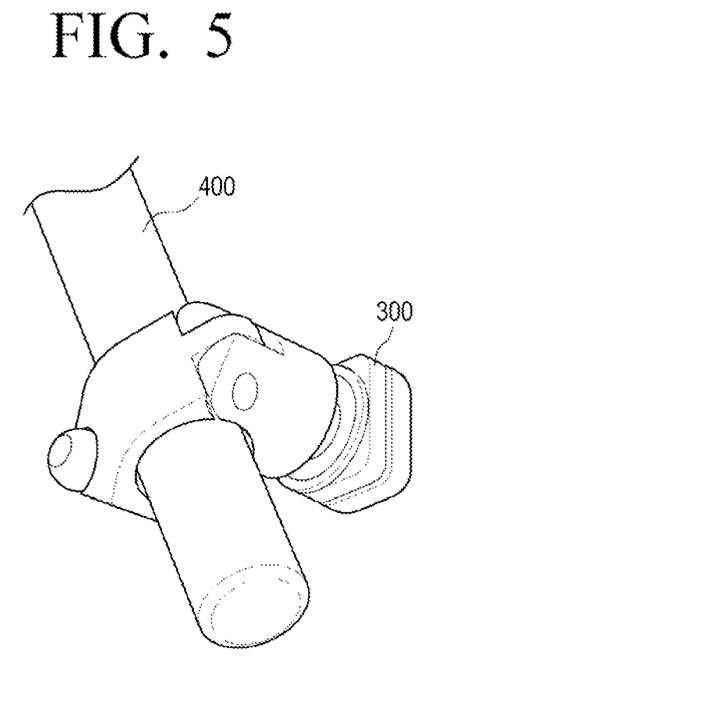
FIG. 5 is a view illustrating a combination between a connection part and an external fixing part according to an exemplary embodiment of the present general inventive concept.

The driver 160 is fixed onto a side of the moveable bone region of the fracture region and moves the moveable bone region. In detail, the driver 160 includes a motor and a robot arm and moves the movable bone region of the fracture region by using the robot arm based on a manipulation command of the manipulator 170 that will be described later. The driver 160 may be connected to the fracture region through a device as shown in FIGS. 3 through 5.

The manipulator 170 has a plurality of functions through which a user may set or select various types of functions supported by the repositioning procedure robot 100. The manipulator 170 receives a control command for controlling an operation of the driver. In the present exemplary embodiment, the display unit 130 and the manipulator 170 are separate elements but may be realized as a device such a touch screen that simultaneously realizes an input and an output.

The path calculator 180 calculates a movement path for repositioning the movable bone region of the fracture region. In detail, the path calculator 180 may calculate a movement path of a bone region of the fracture region for enabling a fractured bone on the three-dimensional fracture image and a normal bone on the three-dimensional normal image to have the same position, by using the three-dimensional normal image and the three-dimensional fracture image. The calculation of the movement path may be performed through an algorithm that is optimized by various types of experiments.

The controller 190 controls elements of the repositioning procedure robot 100. In detail, if a repositioning procedure start command is input, the controller 190 may control the photographing unit 110 to capture the fracture region and the normal region. The controller 190 may also control the image processor 120 to generate a three-dimensional interpolation image of a plurality of bone images and control the display unit 130 to display the generated three-dimensional interpolation image.

Also, the controller 190 may control the path calculator 180 to calculate an interpolation path depending on the generated three-dimensional interpolation image. If a driving command is input through the manipulator 170, the controller 190 may control the driver 160 to perform driving according to the driving command. If the bone region is moved by the driving, the sensor 140 may sense the movement of the bone region, and the controller 190 may update the three-dimensional interpolation image displayed on the display unit 130 according to the sensed movement path.

If a polishing command is input through the manipulator 170, the controller 190 may control the driver 160 to keep a position of the bone region in a current state, i.e., to freeze a state of the motor of the driver 160 (in more detail, to keep a rotation angle of the motor in a current state).

As described above, the repositioning procedure robot 100 according to the present exemplary embodiment generates and displays the three-dimensional interpolation images of the fracture region and the normal region corresponding to the fracture region and displays the three-dimensional interpolation image that is changed in real time in response to a movement of a bone performed in a repositioning procedure. Therefore, the doctor may further easily perform the repositioning procedure. Since the three-dimensional interpolation image is sued as described above, the doctor may further precisely check a rotation state, a reduction state, etc. of a whole bone to perform the repositioning procedure.

FIG. 3 is a view illustrating a shape of a fixing pin according to an exemplary embodiment of the present general inventive concept.

Referring to FIG. 3, a fixing pin 200 is an element that is connected to a bone of the fracture region and the robot arm of the driver 160. In detail, the fixing pin 200 includes a spiral region and a threshold region 220.

The spiral region 210 is a region that is inserted into a fractured bone region. The spiral region may have a length of about 7 cm. However, the present general inventive concept is not limited to a numerical value as described above, and thus the length of the spiral region 210 may depend on a state of the patient.

The threshold region 220 is a protrusion region that enables the fixing pin 200 to be inserted only into a preset part of a bone. The threshold region 220 may have a circular shape, a polygonal shape (a triangular shape, a rectangular shape, or the like). In the illustrated example, the threshold region 220 is positioned at a preset distance from an end part of the spiral region 210 of the fixing pin 200 but may be positioned from the end part of the spiral region 210 to an end part of the fixing pin 200. Also, a diameter of the threshold region 220 is the same but may vary between the end part of the spiral region 210 and the end part of the fixing pin 200.

A shape of the threshold region is a circular shape in the illustrated example, but an external shape of the threshold region may be a polygonal shape based on a central axis of the fixing pin 200. If the shape of the threshold region is the polygonal shape as described above, the threshold region may be easily inserted into the bone through a tool such as a general screwdriver, a screw wrench, or the like without using a particular fixing pin inserting tool. A strength of the threshold region having the polygonal shape may be realized to be stronger than a circular shape.

As described above, the fixing pin 200 according to the present exemplary embodiment includes the threshold region 220 that is inserted only into the preset part of the bone so as to prevent the fixing pine from penetrating the bone.

FIG. 4 is a view illustrating a shape of a connection part according to an exemplary embodiment of the present general inventive concept.

Referring to FIG. 4, a connection part 300 combines the fixing pin 200 with an external fixing part 400. In detail, the connection part 300 includes a first region that may fix the fixing pin on a side and a second region that may fix the fixing part 400 on an other side. In more detail, the connection part 300 may include the first region that may fix the fixing pin on the side, position the pin in the first region, and may be combined with the fixing pin 200 by using a wrench or the like. For example, if an outer shape of the fixing pin 200 is a circular shape, an outer shape of the first region may also be a circular shape. If the outer shape of the fixing pin 200 is a triangular shape, the outer shape of the first region may also be a triangular shape.

The connection part 300 may include the second region that may fix the external fixing part 400 on the other side, position the external fixing part in the second region, and may be combined with the external fixing part 400 by using a wrench or the like. A combination shape between the connection part 300 and the external fixing part 400 is illustrated in FIG. 5. The external fixing part 400 may have at least one selected from a U shape, a ring shape, a semicircular shape, and a linear shape, and thus the second region may have a shape corresponding to an outer shape of the external fixing part 400.

As described above, the external fixing part 400 may be connected to the robot arm of the driver 160 that has been described above. Therefore, the driver 160 may be fixed into a fractured bone through a consecutively connected relation of the external fixing part 400, the connection part 300, and the fixing pin 200 and move a fractured bone region.

Only a connection relation between one external fixing part 400 and one connection part 300 is illustrated in FIG. 5. However, a plurality of fixing pins 200, a plurality of connection parts 300, and a plurality of external fixing pins 400 may be complexly connected to one another in the fractured bone region.

Figure 6:
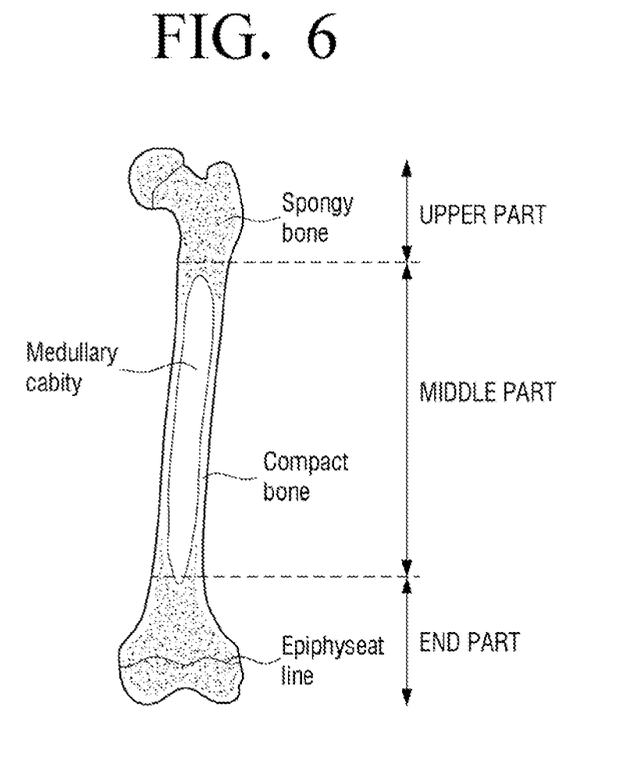
FIG. 6 is a view illustrating a structure of a bone.

FIG. 6 is a view illustrating a structure of a bone.

In detail, the bone shown in FIG. 6 is a femoral bone that may be divided into an upper part (an epiphysis), a middle part (a diaphysis), and an end part (a metaphysis).

If a fracture of the bone occurs in the diaphysis (i.e., in the middle part of the bone), the repositioning procedure robot recognizes a fracture of the diaphysis as a main object. Therefore, an upper region (the epiphysis) and a lower region (the diaphysis) may be used as main indicators in determination and reposition processes of a rotation distortion after the fracture.

Here, the middle region of the bone, i.e., the diaphysis, has a simple curved cylinder shape. Therefore, the image processor 120 may extract parameters, including a length, a diameter, and a bending degree, from each of a plurality of images and generate a three-dimensional interpolation image by using the extracted parameters. As described above, in the present exemplary embodiment, a three-dimensional interpolation image may be generated by using only minimum two bone images. Therefore, a radiation exposure to the patient may be reduced, and the three-dimensional interpolation image may also be applied to a pregnant patient or a pediatric patient.

A three-dimensional interpolation as described above may be performed with respect to a whole part of a bone or may be performed with respect to only a preset region of the bone. In detail, an interpolation may be performed with respect to the epiphysis and the metaphysis, on which the three-dimensional interpolation is difficult to be performed, by using standardized data of general people, and the three-dimensional interpolation may be performed with respect to the middle part (i.e., the diaphysis) that may be relatively easily interpolated.

Figure 8:
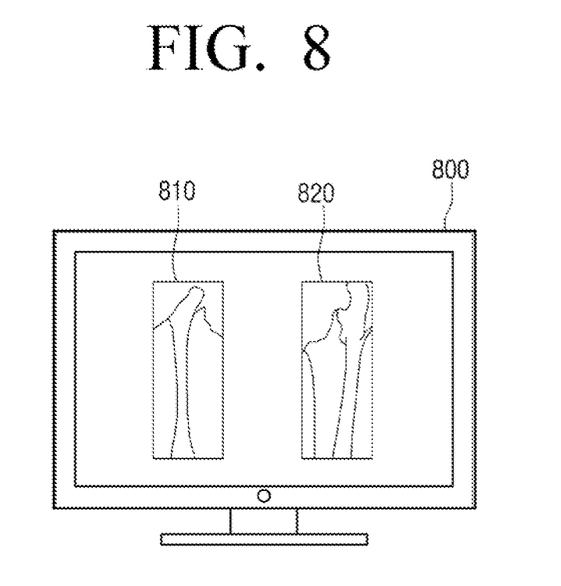

FIGS. 7 through 9 are views illustrating a user interface (UI) window that may be displayed on the display unit of FIG. 1, according to various exemplary embodiments of the present general inventive concept.

Referring to FIG. 7, the UI window overlays a three-dimensional fracture image 720 on a three-dimensional normal image 710. Since the three-dimensional fracture image 720 is overlaid on the three-dimensional normal image as described above, the doctor may further easily check a movement path of a movable bone region 721 of a fracture region. Also, the UI window may be changed in real time by a bone movement.

Here, the UI window may a color, an illumination intensity, a luminance, etc. of the overlaid three-dimensional fracture image 720 differently from the three-dimensional normal image. An overlay degree (i.e., a transparency) and an overlay position of the displayed three-dimensional fracture image may be changed by a manipulation of a user.

As shown in FIG. 7, the three-dimensional fracture image is overlaid on the three-dimensional normal image. However, as shown in FIG. 8, a three-dimensional fracture image 820 and a three-dimensional normal image may not be overlaid with each other but may be separately displayed.

Referring to FIG. 9, a UI window 900 displays an image 910 where a three-dimensional fracture image is overlaid on a three-dimensional normal image as shown in FIG. 7 and displays a matching degree 920 of each region. Since the UI window 900 displays the matching degrees together as described above, the doctor may easily determine whether repositioning is performed, and check a matching degree of each region in a surgical operation process. Therefore, the doctor may check whether there has been rotation, reduction, or overtraction of a whole bone.

Figure 10:
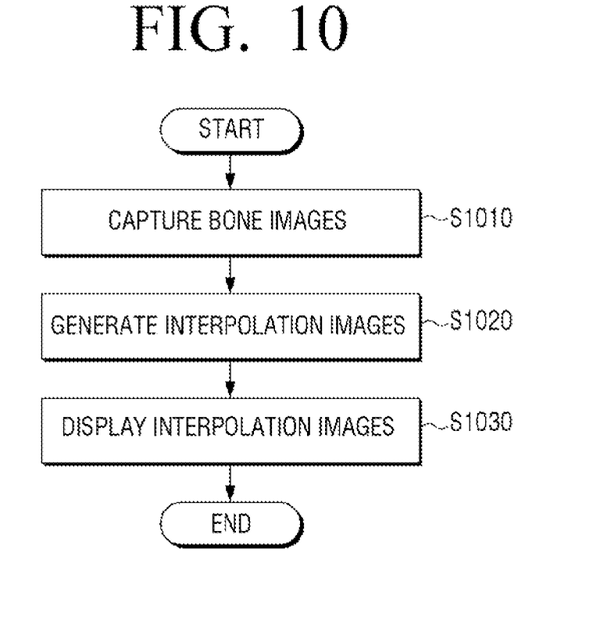
FIG. 10 is a flowchart illustrating a method of controlling an operation of a robot for a repositioning procedure according to an exemplary embodiment of the present general inventive concept.

FIG. 10 is a flowchart illustrating a method of controlling an operation of a repositioning procedure robot according to an exemplary embodiment of the present general inventive concept.

Referring to FIG. 10, in operation S1010, a plurality of bone images of each of a fracture region and a normal region corresponding to the fracture region of a patient are captured at different angles. In detail, each of the fracture region and the normal region corresponding to the fracture region may be rotated to capture the plurality of bone images by using a technology such as X-ray, MRI, or CT that may capture a bone. Here, the normal region is a bone region that is positioned to face a bone positioned in the fracture region. For example, if the fracture region is a left femoral bone, the normal region is a right femoral bone.

In operation S1020, three-dimensional interpolation images of the fracture region and the normal region are generated by using the plurality of bone images that are captured. The operation of generating the three-dimensional interpolation images has been described in detail with reference to FIG. 6, and this a repeated description is omitted.

In operation S1030, the generated three-dimensional interpolation image of the fracture region and the generated three-dimensional interpolation image of the normal region are displayed together. Here, the generated three-dimensional interpolation image of the fracture region may be overlaid on the generated three-dimensional interpolation image of the normal region.

Therefore, the method according to the present exemplary embodiment generates and displays the fracture region and the three-dimensional interpolation image corresponding to the fracture region. Therefore, a doctor may further easily perform a repositioning procedure by using the displayed three-dimensional interpolation image. The method of FIG. 10 may be performed on the repositioning procedure robot 100 having the structure of FIG. 1 or 2 or on the repositioning procedure robot 100 having other types of structures.

A method of controlling an operation of a repositioning procedure robot as described above may be realized as a program including a computer-executable algorithm. The program may be stored and provided on a non-transitory computer readable medium.

The non-transitory computer-readable medium refers to a medium which does not store data for a short time such as a register, a cache memory, a memory, or the like but semi-permanently stores data and is readable by a device. In detail, the above-described applications or programs may be stored and provided on a non-transitory computer readable medium such as a CD, a DVD, a hard disk, a blue-ray disk, a universal serial bus (USB), a memory card, a ROM, or the like.

Figure 11:
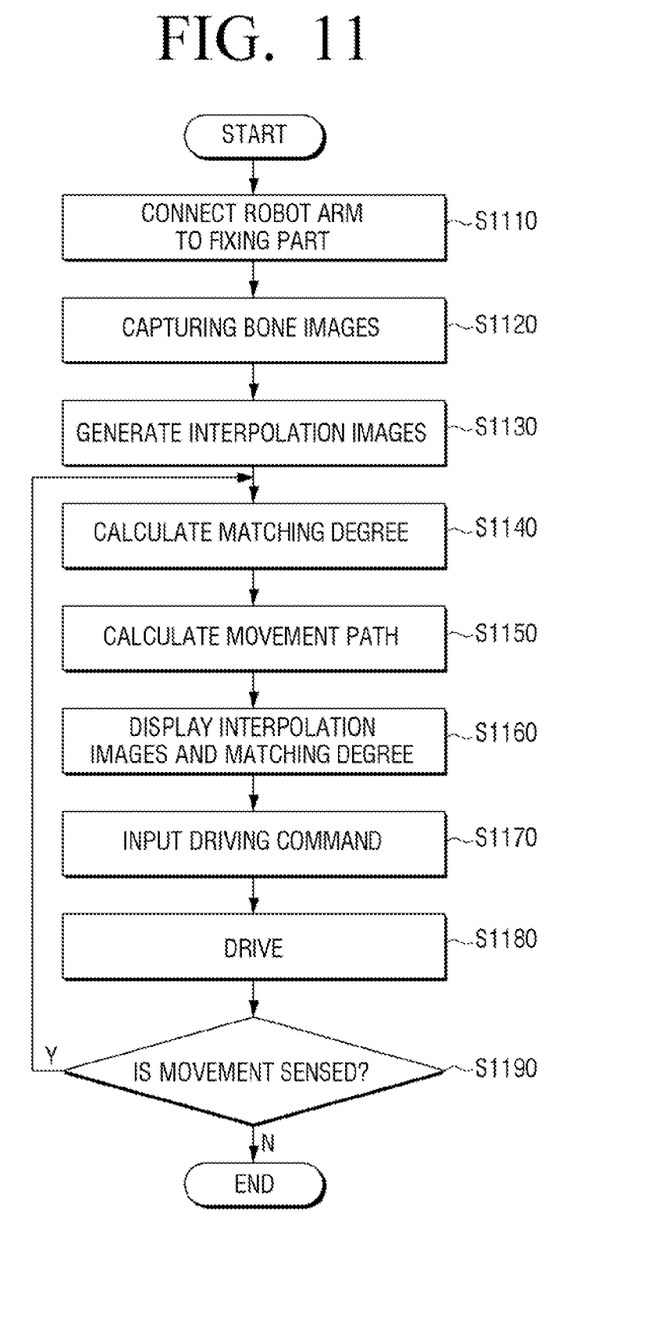
FIG. 11 is a flowchart illustrating the method of FIG. 10 in detail.

FIG. 11 is a flowchart illustrating the method of FIG. 10 in detail.

Referring to FIG. 11, in operation S1110, a doctor connects a robot arm to a fractured region by using a fixing pin, a connection part, and an external fixing part as described with reference to FIGS. 3 through 5.

In operation S1120, a plurality of bone images of each of a fracture region and a normal region corresponding to the fracture region of a patient are captured at different angles. In the exemplary embodiment, the bone images are captured after the operation of connecting the robot arm to the fractured region. However, the operation of connecting the robot arm to the fractured region may be performed after capturing the bone images and generating a three-dimensional interpolation image that will be described later.

In operation S1130, a three-dimensional fracture image and a three-dimensional normal image are generated by using the plurality of bone images that are captured. A process of generating the three-dimensional interpolation image is the same as described with reference to FIG. 6, and thus a repeated description is omitted.

In operation S1140, a matching degree is calculated by using the three-dimensional fracture image and the three-dimensional normal image. In detail, the matching degree may be calculated by using outlines or other parameters (e.g. volumes) of two three-dimensional interpolation images. The calculation of the matching degree may be performed with respect to each of divided regions (e.g., an upper region, a middle region, and a lower region).

A movement path of a movable bone region of the fracture region is calculated by using the three-dimensional fracture image and the three-dimensional normal image that are generated.

In operation S1160, the three-dimensional fracture image and the three-dimensional normal image are displayed. In detail, the three-dimensional fracture image may be overlaid on the three-dimensional normal image. Here, the calculated matching degree may be displayed together.

In operation S1170, a driving command is input from a user (in detail, the doctor). In operation S1180, the robot arm is driven to move the movable bone region of the fracture region.

If the movement of the bone region is sensed by a sensor in operation S1190, operations described above are repeated according to a sensed movement path.

Therefore, the method according to the present exemplary embodiment generates and displays the fracture region and the three-dimensional interpolation image of the normal region corresponding to the fracture region, and displays the three-dimensional interpolation image that is changed in real time in response to the bone movement in a surgical operation process. As a result, the doctor may further easily perform a repositioning procedure. In particular, since the three-dimensional interpolation image is used, the doctor may further precisely check a rotation state, a reduction state, etc. of a whole bone to perform the repositioning procedure. The method of FIG. 11 may be performed on the repositioning procedure robot 100 having the structure of FIG. 2 or on the repositioning procedure robot 100 having other types of structures.

Also, a method of controlling an operation of a repositioning procedure robot as described above may be realized as a program including a computer-executable algorithm. The program may be stored and provided on a non-transitory computer readable medium.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

The invention claimed is:

1. A robot for a repositioning procedure, comprising:
   a photographing unit configured to capture a plurality of bone images of a fracture region and a normal region corresponding to the fracture region of a patient at different angles;
   an image processor configured to generate three-dimensional interpolation images of the fracture region and the normal region by using the plurality of bone images;
   a display unit configured to display the three-dimensional interpolation image of the fracture region and the three-dimensional interpolation image of the normal region together to determine a matching degree between the three-dimensional interpolation image of the fracture region and the normal region; and
   a driver configured to be fixed onto a side of a movable bone region of the fracture region and move the movable bone region, wherein the driver is connected to the side of the movable bone region through a fixing pin, a connection part, and an external fixing part.

2. The robot of claim 1, wherein the photographing unit captures the fracture region and the normal region by using at least one device selected from X-ray, MRI, and CT.

3. The robot of claim 1, wherein the image processor extracts diaphyses of the bone images and generates a three-dimensional interpolation image of the extracted diaphyses.

4. The robot of claim 1, wherein the image processor generates the three-dimensional interpolation image in consideration of at least one selected from diameters, bending degrees, and lengths of the bone images.

5. The robot of claim 1, further comprising:
   a position sensor configured to sense a position of a movable bone region of the fracture region,
   wherein the display unit overlaps the three-dimensional interpolation image of the fracture region on the three-dimensional interpolation image of the normal region based on the sensed position.

6. The robot of claim 1, further comprising:
   a matching processor configured to extract bone outlines of the three-dimensional interpolation image of the fracture region and the three-dimensional interpolation image of the normal region and calculate the matching degree between the extracted bone outlines,
   wherein the display unit displays the calculated matching degree.

7. The robot of claim 6, wherein the matching processor divides the three-dimensional interpolation image into a plurality of regions and calculates matching degrees between bone outlines of the plurality of regions.

8. The robot of claim 1, further comprising:
   a manipulator configured to receive a control command for controlling an operation of the driver.

9. The robot of claim 8, wherein the manipulator receives a stop command as a control command, and in response to the stop command being input, the driver keeps a position of the movable bone region in a current state.

10. The robot of claim 8, further comprising:
    a path processor configured to calculate a movement path for repositioning the movable bone region of the fracture region; and
    a processor configured to stop an operation of the driver in response to the movable bone region straying from the calculated movement path.

11. The robot of claim 1, wherein the fixing pin comprises a spiral region that is inserted into a fractured bone region and a threshold region that protrudes to enable the spiral region to be inserted only into a preset depth.

12. The robot of claim 11, wherein an outer shape of the threshold region is a polygonal shape based on a central axis of the fixing pin.

13. The robot of claim 1, wherein the connection part comprises a first region that fixes the fixing pin on a side and a second region that fixes the external fixing part on an other side.

14. The robot of claim 1, wherein the external fixing part has at least one selected from a U shape, a ring shape, a semicircular shape, and a linear shape.

15. A method of controlling an operation of a robot for a repositioning procedure, the method comprising:
    capturing a plurality of bone images of a fracture region and a normal region corresponding to the fracture region of a patient at different angles;
    generating three-dimensional interpolation images of the fracture region and the normal region by using the plurality of bone images;
    displaying the three-dimensional interpolation image of the fracture region and the three-dimensional interpolation image of the normal region together to determine a matching degree between the three-dimensional interpolation image of the fracture region and the normal region; and
    moving a movable bone region of the fracture region, wherein one side of the movable bone region is connected to a driver through a fixing pin, a connection part, and an external fixing part.

16. The method of claim 15, wherein the fracture region and the normal region are captured by using at least one device selected from X-ray, MRI, and CT.

17. The method of claim 15, wherein diaphyses of the bone images are extracted, and a three-dimensional interpolation image of the extracted diaphyses is generated.

18. The method of clam 15, wherein the three-dimensional interpolation image is generated in consideration of at least one selected from diameters, bending degrees, and lengths of the bone images.

19. The method of claim 15, further comprising:
    sensing a position of a movable bone region of the fracture region,
    wherein the three-dimensional interpolation image of the fracture region overlaps on the three-dimensional interpolation image of the normal region based on the sensed position.

20. The method of claim 15, further comprising:
    extracting bone outlines of the three-dimensional interpolation image of the fracture region and the three-dimensional interpolation image of the normal region and calculating the matching degree between the extracted bone outlines,
    wherein the calculated matching degree is displayed.

21. The method of claim 20, wherein the three-dimensional interpolation image is divided into a plurality of regions, and matching degrees between bone outlines of the plurality of regions are calculated.

22. The method of claim 15, further comprising:
    receiving a control command for controlling an operation of the robot, wherein the a movable bone region of the fracture region is moved according to the control command.

23. The method of claim 22, wherein:
the receiving of the control command comprises: receiving a stop command; and
the moving the movable bone region comprises: keeping a position of the movable bone region in a current state in response to the stop command being received.

24. The method of claim 22, further comprising:
calculating a movement path for repositioning the movable bone region of the fracture region; and
stopping an operation of the robot in response to the movable bone region straying from the calculated movement path.

* * * * *